United States Patent [19]
Abel

[11] Patent Number: 5,998,659
[45] Date of Patent: Dec. 7, 1999

[54] PROCESS AND CATALYST FOR PRODUCING VINYL ACETATE

[75] Inventor: Roland Abel, Corpus Christi, Tex.

[73] Assignee: Celanese GmbH, Germany

[21] Appl. No.: 08/952,543

[22] PCT Filed: May 10, 1996

[86] PCT No.: PCT/EP96/01994

§ 371 Date: Dec. 16, 1998

§ 102(e) Date: Dec. 16, 1997

[87] PCT Pub. No.: WO96/37465

PCT Pub. Date: Nov. 28, 1996

Related U.S. Application Data

[63] Continuation of application No. 08/448,140, May 23, 1995, Pat. No. 5,576,457.

[30] Foreign Application Priority Data

Jun. 27, 1995 [DE] Germany .............................. 195 23 271

[51] Int. Cl.$^6$ ..................................................... C07C 67/05
[52] U.S. Cl. ............................ 560/245; 502/170; 502/328
[58] Field of Search ............................ 560/245; 502/170, 502/328

[56] References Cited

U.S. PATENT DOCUMENTS

| | | |
|---|---|---|
| 3,822,308 | 7/1974 | Kronig et al. . |
| 4,231,897 | 11/1980 | Antos . |
| 4,290,921 | 9/1981 | Antos ...................................... 252/442 |
| 4,312,792 | 1/1982 | Antos ...................................... 252/466 |
| 5,011,980 | 4/1991 | Sano ........................................ 560/245 |
| 5,576,457 | 11/1996 | Abel ........................................ 560/245 |

FOREIGN PATENT DOCUMENTS 0634214   1/1995   European Pat. Off. .

*Primary Examiner*—Michael L. Shippen
*Attorney, Agent, or Firm*—Bierman, Muserlian and Lucas

[57] ABSTRACT

The invention relates to a catalyst and a process for preparing vinyl acetate in the gas phase from ethylene, acetic acid and oxygen or oxygen-containing gases over a catalyst comprising palladium and/or its compounds, cadmium compounds and alkali metal compounds on a support, wherein the catalyst additionally contains at least one rhenium and/or at least one zirconium compound.

4 Claims, No Drawings

PROCESS AND CATALYST FOR PRODUCING VINYL ACETATE

This is a continuation application of application Ser. No. 08/448,146, filed May 23, 1995, now U.S. Pat. No. 5,576,457.

It is known that ethylene can be reacted in the gas phase with acetic acid and oxygen or oxygen-containing gases over fixed-bed catalysts containing palladium/cadmium/alkali metal to give vinyl acetate. In this process, a space-time yield of more than 200 g/l.h is obtained (U.S. Pat. No. 3 939 199, U.S. Pat. No. 4 668 819, U.S. Pat. No. 4 902 823, EP-A-0 403 950, U.S. Pat. No. 5 225 388, EP-A-0 565 952, EP-A-0 634 208, EP-A-0 634 209, EP-A-0 634 214).

It has now surprisingly been found that such catalysts are considerably improved by addition of at least one rhenium and/or at least one zirconium compound, i.e. they give a higher space-time yield at the same or higher selectivity of the vinyl acetate synthesis and are more slowly deactivated.

The invention accordingly provides a process for preparing vinyl acetate in the gas phase from ethylene, acetic acid and oxygen or oxygen-containing gases over a catalyst comprising palladium and/or its compounds, cadmium compounds and alkali metal compounds on a support, wherein the catalyst additionally contains at least one rhenium and/or at least one zirconium compound.

The invention further provides a catalyst comprising palladium and/or its compounds, cadmium compounds and alkali metal compounds on a support, wherein the catalyst additionally contains at least one rhenium and/or at least one zirconium compound.

Suitable supports are the known inert support materials such as silica, aluminum oxide, aluminosilicates, silicates, titanium oxide, zirconium oxide, titanates, silicon carbide and carbon. Particularly suitable are supports of this type having a specific surface area of from 40 to 350 $m^2/g$ (measured by the BET method) and a mean pore radius of from 50 to 2000 Å (measured using mercury porosimetry), especially silicas ($SiO_2$) and $SiO_2/Al_2O_3$ mixtures. These supports are used in the form of spheres, pellets, rings, stars or particles of another shape whose diameter or length and thickness is generally from 3 to 9 mm.

The total pore volume of the support is preferably 0.4–1.2 ml/g, and less than 10% of this volume should be formed by "micropores" having a pore diameter of below 30 Å (Angstrom). Such supports can be prepared from aerogenic $SiO_2$ or an aerogenic $SiO_2/Al_2O_3$ mixture which is in the form of vitreous microspheres which can be prepared, for example, by flame hydrolysis of silicon tetrachloride or a silicon tetrachloride/aluminum trichloride mixture in a hydrogen/oxygen flame (U.S. Pat. No. 3 939 199). These microspheres are commercially available under the names ®Aerosil or ®Cabosil.

Particular preference is given to the use of a support comprising $Sio_2$ or a $SiO_2/Al_2O_3$ mixture having a surface area of 50–250 $m^2/g$ and a pore volume of 0.4–1.2 ml/g and pressed from such microspheres using organic fillers (EP-A-0 403 950). The particles of this support have a particle size of from 4 to 9 mm, with from 5 to 20% of the pore volume of the support being formed by pores having radii of from 200 to 3000 Å and from 50 to 90% of the pore volume being formed by pores having radii of from 70 to 100 Å. It is particularly advantageous if these support particles are prepared from the microspheres by tabletting or extrusion with addition of one or more $C_2$–$C_{20}$-carboxylates of Li, Mg, Al, Zn, Fe or Mn as binders and with addition of organic fillers (such as sugar, urea, higher fatty acids, relatively long chain paraffins, microcrystalline cellulose) and lubricants (such as kaolin, graphite, metal soaps) (U.S. Pat. No. 5 225 388). The particles are subsequently ignited in $O_2$-containing gases at about 500–900° C. for about 0.25–5 hours.

The catalytically active substances can be applied to the support in a customary manner, for example by single or multiple impregnation of the support with a solution of the active substances, subsequent drying and, if desired, reduction. However, the active substances can also be applied to the support by, for example, single or multiple spraying on, vapor deposition or dipping or by precipitation onto the support.

Suitable solvents for the catalytically active substances are, in particular, water or unsubstituted carboxylic acids having from 2 to 10 carbon atoms, for example acetic acid, propionic acid, n- and iso-butyric acid and the various valeric acids. Owing to its physical properties and also for economic reasons, preference is given to using acetic acid as carboxylic acid. The additional use of an inert solvent is advantageous when the carboxylic acid used is one in which the substances are not sufficiently soluble. Thus, for example, palladium chloride can be dissolved significantly better in aqueous acetic acid than in glacial acetic acid. Suitable additional solvents are those which are inert and miscible with the carboxylic acid, for example water or ethers such as tetrahydrofuran or dioxane, but also hydrocarbons such as benzene.

It is possible to prepare either fully impregnated catalysts in which the catalytically active metal compounds have penetrated to the core of the support particles or else surface-impregnated catalysts in which the metal salts have not penetrated to the core but only into a more or less thick outer part of the support particles, i.e. the surface zone of the particles. In both cases, the elements to be applied can be applied individually in the form of solutions of their compounds, or else in any combinations. Preference is given to using solutions containing at least one compound of each of the elements to be applied. Particular preference is given to using a single solution containing exactly one compound of each of the elements to be applied. If "the solution" is referred to below, this means a solution containing at least one compound of one of the elements Pd, alkali metal, Cd, Re, Zr, or a solution containing at least one compound of each of two or more of these elements.

To prepare fully impregnated catalysts, the procedure is preferably as follows (U.S. Pat. No. 4 902 823, U.S. Pat. No. 3 393 190, U.S. Pat. No. 4 668 819):

The impregnation of the catalyst support with the solution of the active components is undertaken in such a way that the support material is covered with the solution and any excess solution is then poured off or filtered off. In consideration of solution losses, it is advantageous to use only the amount of solution corresponding to the integral pore volume of the catalyst support and to mix carefully so that the particles of the support material are uniformly wetted. It is advantageous to carry out the impregnation process and the mixing at the same time, for example in a rotating drum or a tumble dryer, with drying being able to follow immediately. Furthermore, it is generally advantageous to make the composition of the solution used for impregnating the catalyst support such that the desired amount of active substances is applied by a single impregnation. However, this amount can also be applied by a plurality of impregnations, with drying preferably being carried out after each impregnation.

To prepare surface-impregnated catalysts, preference is given to proceeding according to one of the following three methods, where a solution of at least one compound of at least one of the elements Pd, alkali metal, Cd, Re and/or Zr having a dynamic viscosity of at least 0.003 Pa.s, preferably from 0.005 to 0.009 Pa.s is always used:

1. The support particles are, while being intimately mixed, sprayed once or a plurality of times with the solution in the form of droplets having an average diameter of at least 0.3 mm or in the form of liquid jets and are immediately dried after each spraying. "Immediate" drying here means that drying of the sprayed particles has to be commenced promptly. It is here generally sufficient if the drying of the particles is commenced at the latest within 30 minutes of the end of a spraying. On each spraying, the solution volume is from 5 to 80% of the pore volume of the support particles. This method is comprehensively described in EP-A-0 634 214, which is hereby expressly incorporated by reference.

2. The support particles are, while being intimately mixed, impregnated once or a plurality of times with the solution and immediately dried after each impregnation. "Immediate" drying here means the same as in the 1st method, and the solution volume in each impregnation is from 5 to 80% of the pore volume of the support particles. This method is comprehensively described in EP-A-0 634 209, which is hereby likewise expressly incorporated by reference.

3. The support particles are impregnated once or a plurality of times with the solution and dried after each impregnation, but, in contrast to the 2nd method, no upper limit is placed on the solution volume: it is now more than 80% of the pore volume in each impregnation. Owing to the larger solution volume, intimate mixing is not absolutely necessary, although generally useful. Instead, the duration of each impregnation and the time until the subsequent drying is commenced, i.e. the time from the commencement of each impregnation until the commencement of the subsequent drying, now has to be sufficiently short for, after completion of the last drying, a surface zone of 5–80% of the pore volume of the support particles to contain the catalytically active elements. The length of this time which has to be selected for this purpose can easily be determined by preliminary experiments. This method is comprehensively described in EP-A-0 634 208, which is hereby likewise expressly incorporated by reference.

A suitable method of determining the thickness of the surface zone achieved in the surface-impregnated catalysts prepared comprises cutting open a representative number of impregnated and dried support particles and measuring the thickness of the surface zone under the microscope. Here, preferably less than 5% of the particles should have a surface zone thickness which deviates by more than 15% from the desired value.

The drying of the impregnated or sprayed catalyst support is preferably carried out under reduced pressure (from 0.1 to 0.8 bar), both in the case of fully impregnated catalysts and in the case of surface-impregnated catalysts. The temperature during drying should generally be from 50 to 80° C., preferably from 50 to 70° C. Furthermore, it is generally advisable to carry out the drying in a stream of inert gas, for example in a stream of nitrogen or carbon dioxide. The residual solvent content after drying should preferably be less than 8% by weight, in particular less than 6% by weight.

The finished catalysts should contain the following amounts of the catalytically active elements:

The palladium content is generally from 0.6 to 3.5% by weight, preferably from 0.8 to 3.0% by weight, in particular from 1.0 to 2.5% by weight.

The alkali element content is generally from 0.3 to 10% by weight.

Preference is given to using potassium, generally in an amount of from 0.5 to 4.0% by weight, preferably from 1.0 to 3.0% by weight, in particular from 1.5 to 2.5% by weight.

The cadmium content is generally from 0.1 to 2.5% by weight, preferably from 0.4 to 2.5% by weight, in particular from 1.3 to 2% by weight.

The content of rhenium or zirconium is generally from 0.05 to 3% by weight, preferably from 0.05 to 1% by weight, in particular from 0.05 to 0.5% by weight. Rhenium and zirconium can also be present together in the catalyst, in which case the total content of the two elements is within the specified ranges.

The percentages indicated always refer to the amounts of the elements Pd, alkali element, Cd, Zr and/or Re present in the catalyst, based on the total mass of the catalyst (active elements plus anions plus support material).

Suitable compounds for application to the support are all compounds of palladium, cadmium, an alkali metal, rhenium and zirconium which are soluble and contain no constituents which poison the catalyst, for example sulfur; preference is given to the acetates and the chlorides. However, in the case of chlorides it has to be ensured that the chloride ions are removed before use of the catalyst for the synthesis of vinyl acetate. This is achieved by washing the doped support, e.g. with water, after, for example, the palladium applied as chloride has been converted into an insoluble form, for instance by reduction and/or by precipitation with hydroxides.

Particularly suitable compounds of palladium are the carboxylates, preferably the salts of aliphatic monocarboxylic acids having from 2 to 5 carbon atoms, for instance the acetate, the propionate or the butyrate. Further examples of suitable compounds are the nitrate, nitrite, hydrated oxide, oxalate, acetylacetonate, acetoacetate. Owing to its good solubility and availability, palladium acetate is the particularly preferred palladium compound.

As alkali metal compound, preference is given to using at least one K, Rb or Cs compound, in particular at least one K compound. Particularly suitable compounds are carboxylates, in particular acetates and propionates. Also suitable are compounds which are converted into the acetate under the reaction conditions, for instance the hydroxide, the oxide or the carbonate.

As cadmium compound, the acetate is particularly suitable.

Particularly suitable zirconium compounds are the acetate and the acetylacetonate.

Particularly suitable rhenium compounds are $Re_2O_7$ and $(NH_4)ReO_4$.

If reduction of the palladium compound is carried out, which is sometimes useful, a gaseous reducing agent can be used for this purpose. Suitable reducing agents are, for example, hydrogen, methanol, formaldehyde, ethylene, propylene, isobutylene, butylene and other olefins. The reduction temperature is generally between 40 and 260° C., preferably between 70 and 200° C. It is generally advantageous to use a reducing agent diluted with inert gas and containing from 0.01 to 50% by volume, preferably from 0.5 to 20% by volume, of reducing agent. Inert gases which can be used are, for example, nitrogen, carbon dioxide or a noble gas. The amount of the reducing agent depends on the amount of palladium; the reduction equivalent should be at least from 1 to 1.5 times the oxidation equivalent, but larger amounts of reducing agent do no harm. The reduction is carried out subsequent to drying.

The preparation of vinyl acetate is carried out by passing acetic acid, ethylene and oxygen or oxygen-containing gases at temperatures of from 100 to 220° C., preferably from 120 to 200° C., and at pressures of from 1 to 25 bar, preferably from 1 to 20 bar, over the finished catalyst, with unreacted components being able to be circulated. The oxygen concentration is advantageously kept below 10% by volume (based on the gas mixture free of acetic acid). However, sometimes dilution with inert gases such as nitrogen or carbon dioxide is advantageous. Carbon dioxide is particularly suitable for dilution in the case of a circulation procedure, since it is formed in small amounts during the reaction.

By means of the catalysts of the invention, a higher space-time yield and an equal or higher selectivity at a longer operating life of the catalyst is achieved than with catalysts which contain no rhenium or zirconium.

The following examples illustrate the invention. The percentages of the elements Pd, Cd, Zr, Re and K are percentages by weight based on the total mass of the catalyst.

As catalyst support, $SiO_2$ was used in the form of pellets having a diameter of 6 mm and a height of 6 mm. The pellets had been pressed from ®Aerosil powder with the aid of magnesium stearate as binder as described in U.S. Pat. No. 5 225 388. The surface area of the support was 120 m²/g, its pore volume was 0.784 ml/g and its bulk density was 500 g/l. The pore volume of 1 l of support was 392 ml.

I. Fully impregnated catalysts

Comparative Example 1

1 l of silica supports were impregnated at 60° C. with a solution of 24.3 g of palladium acetate, 21.3 g of cadmium acetate and 23.8 g of potassium acetate in 392 ml of glacial acetic acid (solution volume=100% of the pore volume of the support). Subsequently, the supports were dried in a drying oven at 200 mbar under nitrogen until the residual acetic acid content was 6% by weight; the drying temperature was 65° C. The finished catalyst contained 2.3% by weight of Pd, 1.8% by weight of Cd and 1.9% by weight of K. It was completely impregnated, i.e. into the core.

50 ml of this catalyst were placed in a reaction tube having an internal diameter of 8 mm and a length of 1.5 m. Then, at a pressure of 8 bar (reactor inlet) and a catalyst temperature of 150° C., the gas to be reacted was passed over the catalyst for a number of days. This gas consisted of 27% by volume of ethylene, 55% by volume of nitrogen, 12% by volume of acetic acid and 6% by volume of oxygen. The results are shown in Table 1. In this table, "relative rate of output decrease" is the quotient of output decrease (=initial output of the experiment minus final output of the experiment) and duration of the experiment, relative to the quotient of the catalyst used in Comparative Example 1. This catalyst thus has the quotient (=relative rate of output decrease) 1.

EXAMPLE 1a

The procedure was as in Comparative Example 1, except that the solution additionally contained 7.5 g of zirconium acetylacetonate and the amount of glacial acetic acid was 389 ml. The results are shown in Table 1.

EXAMPLE 1b 1 l of the catalyst prepared as in Comparative Example 1 was impregnated at room temperature with a solution of 4.2 g of $Re_2O_7$ in 308 ml of water (solution volume=100% of the pore volume of the catalyst). The catalyst was subsequently dried as in Comparative Example 1, until a residual water content of 6% by weight had been reached. The catalyst was tested as in Comparative Example 1. The results are shown in Table 1.

TABLE 1

| | (Fully impregnated catalysts) | | |
| --- | --- | --- | --- |
| | Output* (g/lh) | Selectivity (%) | Relative rate of output decrease |
| Comparative Example 1 | 813 | 94.3 | 1 |
| Example 1a | 870 | 94.5 | 0.7 |
| Example 1b | 840 | 94.8 | 0.7 |

* Initial output (gram of vinyl acetate per liter of catalyst and hour)

II. Surface-impregnated catalysts

Comparative Example 2

At 65° C., 25.3 g of palladium acetate, 25 g of cadmium acetate and 25.3 g of potassium acetate were dissolved in 130.0 ml of anhydrous acetic acid (glacial acetic acid) (solution volume=33% of the pore volume) and the highly viscous solution (7 mpa.s) was placed in a vessel preheated to 65° C. 1 l of catalyst supports was likewise heated to 65° C. and placed in a flask. The entire impregnation solution was then poured over the support particles and the particles were intimately mixed until the solution had been completely absorbed by the particles. This procedure was complete after 3 minutes.

The catalyst was subsequently dried as in Comparative Example 1. The finished catalyst contained 2.3% by weight of Pd, 1.8% by weight of Cd and 1.9% by weight of K. The thickness of the surface zone was 0.8 mm.

Testing was carried out as in Comparative Example 1. The results are shown in Table 2. The "relative rate of output decrease" is defined as in Comparative Example 1, i.e. again relative to the catalyst used there.

EXAMPLE 2a

The procedure was as in Comparative Example 2, except that the solution additionally contained 7.0 g of zirconium acetylacetonate. The thickness of the surface zone was 0.8 mm. The results are shown in Table 2.

EXAMPLE 2b 1 l of the catalyst as prepared in Comparative Example 2 was impregnated at room temperature with a solution of 3.5 g of $Re_2O_7$ in 300 ml of water (solution volume =100% of the pore volume of the catalyst). The catalyst was subsequently dried as in Comparative Example 1, until a residual water content of 6% by weight had been reached. The catalyst was tested as in Comparative Example 1. The results are shown in Table 2.

TABLE 2

(Surface-impregnated catalysts)

|  | Output* (g/lh) | Selectivity (%) | Relative rate of output decrease |
|---|---|---|---|
| Comparative Example 2 | 922 | 95.8 | 1.4 |
| Example 2a | 950 | 96.1 | 0.9 |
| Example 2b | 940 | 96.0 | 1.0 |

* Initial output (gram of vinyl acetate per liter of catalyst and hour)

I claim:

1. A supported catalyst comprising palladium, and/or its compounds, cadmium and alkali metal compounds on a support, wherein the catalyst additionally contains at least one zirconium compound in amounts, calculated on an elemental basis, corresponding to 0.5 to 3% by weight and optionally 0.05 to 3% by weight of at least one rhenium compound based on the total mass of the catalyst, and, if the catalyst comprises palladium and/or its compounds, cadmium and at least one rhenium compound, the alkali metal compound has to be a potassium compound.

2. A catalyst as claimed in claim 1, wherein the catalyst contains at least one potassium compound.

3. A catalyst as claimed in claim 1, wherein the catalyst contains from 0.05% by weight to 1% by weight of zirconium, based on the total mass of the catalyst.

4. A catalyst as claimed in claim 1, wherein the catalyst contains from 0.05% by weight to 0.5% by weight of zirconium, based on the total mass of the catalyst.

* * * * *